United States Patent
Hynansky

[11] Patent Number: 6,139,144
[45] Date of Patent: Oct. 31, 2000

[54] COLD WEATHER EYEGLASS SYSTEM WITH PROTECTIVE SHIELD

[75] Inventor: Deanna Hynansky, Greenville, Del.

[73] Assignee: Hawaiko, Inc., Greenville, Del.

[21] Appl. No.: 09/409,702

[22] Filed: Oct. 1, 1999

[51] Int. Cl.[7] .................................................. G02C 1/00
[52] U.S. Cl. ............................................ 351/158; 351/52
[58] Field of Search ................................. 351/41, 51, 52, 351/158, 122

[56] References Cited

U.S. PATENT DOCUMENTS

| | | | |
|---|---|---|---|
| 3,526,450 | 9/1970 | Berry | 351/52 |
| 3,952,331 | 4/1976 | Melville | 2/14 |
| 4,105,304 | 8/1978 | Baker | 351/47 |
| 4,692,002 | 9/1987 | Meistrell | 351/156 |
| 4,707,863 | 11/1987 | McNeal | 2/436 |
| 4,934,807 | 6/1990 | Bollé et al. | 351/62 |
| 5,092,667 | 3/1992 | Bagley | 351/156 |
| 5,191,363 | 3/1993 | Smith et al. | 351/62 |
| 5,191,364 | 3/1993 | Kopfer | 351/62 |
| 5,321,443 | 6/1994 | Huber et al. | 351/47 |
| 5,339,119 | 8/1994 | Gardner | 351/158 |
| 5,402,189 | 3/1995 | Gill | 351/44 |
| 5,524,291 | 6/1996 | Rio et al. | 2/13 |
| 5,528,800 | 6/1996 | Kliot | 24/3.3 |
| 5,614,963 | 3/1997 | Parker | 351/47 |
| 5,644,800 | 7/1997 | Leonardi | 2/431 |
| 5,701,892 | 12/1997 | Bledstein | 351/47 |
| 5,704,068 | 1/1998 | Martin | 2/173 |
| 5,771,500 | 6/1998 | Mayers | 2/452 |

OTHER PUBLICATIONS

The Optican, "Fur Topped Eyewear", vol. 129, Feb. 18, 1955.

*Primary Examiner*—Huy Mai
*Attorney, Agent, or Firm*—Convolly Bove Lodge & Hutz LLP

[57] ABSTRACT

An eyeglass system comprising conventional eyeglasses and a cold weather protective shield in either one combined unit or in a removable form. The present invention is particularly directed towards people who suffer from chronic sinusitis. The shield component may be integrally attached to the eye glass frame or be releasably attached to a standard-style eyeglass frame (either of which can be fitted with standard size and shape prescription lenses), to provide protection against cold weather. The preferred embodiment of the removable assembly includes a one-piece member having side retaining members with the member serving as the frame, side retaining members, and a top retaining member.

6 Claims, 1 Drawing Sheet

COLD WEATHER EYEGLASS SYSTEM WITH PROTECTIVE SHIELD

BACKGROUND OF THE INVENTION

The present invention relates to a shield that may be either integrally or removably attached to a standard-style eyeglass frame (which thus can be fitted with standard size and shape prescription lenses) to provide protection against cold weather. The present invention is particularly directed towards people who suffer from chronic sinusitis.

Sinuses are hollow air spaces, of which there are many in the human body. Here, sinuses refer to four pair of paranasal cavities located within the skull or bones of the head surrounding the nose. These include the frontal sinuses over the eyes in the brow area, the maxillary sinuses inside each cheekbone, the ethmoids just behind the bridge of the nose and between the eyes, and behind them, the sphenoids in the upper region of the nose and behind the eyes, all of which develop as outpouchings of the nasal mucosa. They remain connected to the nasal cavity for the free exchange of air and mucus via a narrow ostia with a lumen diameter of 1 to 3 mm, and each is joined with the nasal passages by a continuous mucous membrane lining, the mucoperiosteum. Scientists have not yet determined the function of these paranasal sinuses. It is theorized that sinuses serve functions of making mucus, a fluid that helps warm the air people breathe and add moisture to it, lightening of the skull, improvement of vocal resonance, absorption of shock to the face or skull, and secretion of mucus to assist with air filtration. Hair cells—cilia—continually sweep mucus out of the sinuses into your nose.

Sinusitis, or inflammation of the sinuses, is a common ailment. Some 16 percent of the U.S. population are reported to be diagnosed with sinusitis annually, and chronic sinusitis reportedly affects an estimated 32 million people in the United States. Air trapped within an obstructed sinus, along with pus or other secretions, may cause pressure on the sinus wall. The result is the some times intense pain of a sinus attack. Similarly, when air is prevented from entering a paranasal sinus by a swollen membrane at the opening, a vacuum can be created that also causes pain. Anything that blocks the sinus openings or keeps the cilia from moving can cause a sinus infection, or acute sinusitis. For example, anything that causes a swelling in the nose—an infection or an allergic reaction—can affect the sinuses. A number of factors can contribute to the development of sinusitis. The most common cause of acute bacterial sinusitis is a viral upper respiratory infection. Viruses can enter the body through the nasal passages and set off a chain reaction resulting in sinusitis. For example, the nose reacts to an invasion by viruses that cause infections such as the common cold, flu, or measles by producing mucus and sending white blood cells to the lining of the nose, which congest and swell the nasal passages. When this swelling involves the adjacent mucous membranes of the sinuses, air and mucus are trapped behind the narrowed openings of the sinuses. If the sinus openings become too narrow to permit drainage of the mucus, then bacteria, which normally are present in the respiratory tract, begin to multiply. Most apparently healthy people harbor bacteria, such as *Streptococcus pneumoniae* and *Haemophilus influenzae*, in their upper respiratory tracts with no ill effects until the body's defenses are weakened or drainage from the sinuses is blocked by a cold or other viral infection. The bacteria that may have been living harmlessly in the nose, throat, or sinus area can multiply and cause an acute sinus infection. Chronic inflammation of the nasal passages (rhinitis) also can lead to sinusitis. Allergic rhinitis or hay fever is the most common cause of chronic sinusitis and is a frequent cause of acute sinusitis. Vasomotor rhinitis, caused by humidity, cold air, alcohol, perfumes, and other environmental conditions, also can result in a sinus infection.

Various other causes or contributing factors have been proposed and considered, including the following: Air pollution and cigarette smoke; Nasal or dental procedures; Traveling at high altitudes or swimming under water; Hormone changes that come with puberty; Pregnancy or aging; Sinus blockages; and Immune disorders, such as diabetes or AIDS.

There are two types: acute sinusitis, a short-term condition that responds well to antibiotics and decongestants; and chronic sinusitis which refers to inflammation of the sinuses that continues for weeks, months, or even years. As noted above, allergies are the most common cause of chronic sinusitis. Inhalation of airborne allergens, such as dust, mold, and pollen, often set off allergic reactions (allergic rhinitis) that, in turn, may contribute to sinusitis. As body cells react against these inhaled substances, they release chemical compounds, such as histamine, at the mucosal surface. These chemicals then cause the nasal passages to swell and block drainage from the sinuses, resulting in sinusitis. Damp weather, especially in colder northern temperate climates, also can affect people subject to chronic sinusitis. Victims of chronic sinusitis may have the following symptoms for 12 weeks or more: facial pain/pressure, facial congestion/fullness, nasal obstruction/blockage, nasal discharge/discolored postnasal drainage, pus in the nasal cavity, and at times, fever. They may also have headache, bad breath, fatigue, dental pain, and the production of thick nasal discharge.

Sinusitis has its own localized pain signals, depending upon the particular sinus affected. Since the ethmoid sinuses are near the tear ducts in the corner of the eyes, inflammation of these cavities often causes swelling of the eyelids and tissues around the eyes and pain between the eyes. Exposure to cold increases the facial pain of ethmoid sinusitis. Such facial pain can be increased when plastic or metal frames become cold and hard against the face in winter.

A doctor can prescribe a course of treatment that will clear up the source of the inflammation and relieve the symptoms. Sinusitis is treated by re-establishing drainage of the nasal passages, controlling or eliminating the source of the inflammation, and relieving the pain. Doctors generally recommend decongestants to reduce the congestion, antibiotics to control a bacterial infection, if present, and pain relievers to reduce the pain.

Although sinus infection cannot be cured by home remedies, people can use them to lessen their discomfort. Inhaling steam from a vaporizer or a hot cup of water can soothe inflamed sinus cavities. Another treatment is saline nasal spray, which can be purchased in a pharmacy. Salt water nasal rinses provide short-term relief of congestion by removing crusts and secretions. A hot water bottle; hot, wet compresses; or an electric heating pad applied over the inflamed area also can be comforting. Warm moist air may alleviate sinus congestion. A vaporizer or steam from a pan of boiled water are both recommended. Usual medical advice for sufferers includes the suggestion to apply moist heat by holding a hot, wet compresses against the face to relieve pain in the nose and sinuses.

There does not appear to be any prior art solution to the problem that common eyeglasses in cold weather may themselves contribute to facial pain particularly in case of frontal or ethmoid sinusitis, and the need for a stylish protection that persons would wear in public. There is a common problem of resistance to wear unattractive articles in public. Resistance to use of unwieldy or unbecoming articles in public endangers people with sinusitis, and may restrict outdoor ventures by people who need protection. A convenient, comfortable, secure, fashionable, durable cold weather shield is needed to assist victims of sinusitis to endure cold weather.

DESCRIPTION OF RELATED ART

Many attempts have also been made to provide convenient to wear and use sun shields which will attach to conventional prescription eyeglasses to provide protection from the ultraviolet and infrared rays from the sun. See, for example, U.S. Pat. No. 5,614,963 to Parker, published, Mar. 25, 1997, which describes a sun shield system for protecting the eyes from UV and infrared rays; U.S. Pat. No. 5,524,291 to Rio, published Jun. 11, 1996, for a sun visor for eye glasses; and U.S. Pat. No. 5,321,443 to Huber, published Jun. 14, 1994, which describes a removable sunglass assembly for attachment to a conventional eyeglasses. Side shields are described in, for example, U.S. Pat. No. 4,105,304 to Baker, published Aug. 8, 1978, for Side glare-eliminating device for securement to eyeglasses and other suitable mounting structures, and U.S. Pat. No. 5,402,189 to Gill, published Mar. 28, 1995, for Side shield for eyeglasses and method of making the same. Various combinations of glass lenses and headband assemblies are also described, as shown, for example, in U.S. Pat. No. 5,771,500 to Mayes, published Jun. 30, 1998, for Headband with lens piece.

The prior art has shown various face masks and cowls to protect the face against cold weather. See, for example, the common ski masks and U.S. Pat. No. 5,701,892 to Bledstein and U.S. Pat. No. 5,704,068 to Martin. The prior art also contains numerous disclosures of different types of goggles. Goggles, however, are in general too large, cumbersome, awkward and difficult to wear, to be used outside of specialized activities such as skiing or swimming. Prior art devices such as those disclosed in U.S. Pat. No. 1,669,229 Cook, U.S. Pat. No. 1,677,747, U.S. Pat. No. 1,936,746 Baker, and U.S. Pat. No. 1,754,694 Neuwirth attempted to modify eyeglasses to provide all weather goggle-like eye protection while retaining the appearance and advantages of eyeglasses. These prior art devices were fitted with rubber, foam or some other non-rigid substance around the inside perimeter of the eyeglasses in an attempt to form an acceptable seal. However, as the non-rigid material easily deformed, it would not necessarily retain its resiliency and its shape after multiple uses, and would thereby become ineffective after a short period of time. Moreover, unlike eyeglasses, goggles are customarily held in place by an elastic or adjustable head band. Goggles use a strap around the wearer's head, as the frame is flexible; goggles do not support temple bars because of their non-rigid frame. The head band is attached, at both ends, to the goggle mask which is bent around the wearer's face. Although goggles form a shielding seal around the face, goggles are not a preferred form of eyewear; goggles are typically large, non-rigid, bulky, awkward, and uncomfortable to the wearer.

U.S. Pat. No. 5,339,119 to Gardner, published Aug. 16, 1994, "Eye protection device comprising a foam rubber-like resilient insert member", discloses structures made of one foam component or of two components: an outer shell which can be made of a polyurethane material and a foam rubber-like insert member which components are joined together to form a unitary structure which structure receives the user's eyeglasses therein for the receipt and engagement of the user's existing prescription eyeglasses or non-prescription eyewear, such as sunglasses, to provide a barrier around the area of the user's face enclosed by the structure of this invention. The proposed goggle-like structure may potentially be suitable for sport uses, but suffers from the same problems as do other goggles in that they are designed for specific sport applications and are too bulky and awkward for normal daily use. Similar comments apply to other such disclosure such as U.S. Pat. No. 3,952,331 to Melville, published Apr. 27, 1976, "Protective eye shade for sportsmen"; U.S. Pat. No. 5,191,364 to Kopfer, published, Mar. 2, 1993, "Protective eyewear for use in sports and the like"; and U.S. Pat. No. 4,934,807 to Bolle, published Jun. 19, 1990, "Sunglasses having detachable absorber strip."

SUMMARY OF INVENTION, OBJECTS AND ADVANTAGES

The above mentioned problems are obviated by the present invention which provides a composite eyeglass system, particularly for people who wear prescription eyeglasses, which comprises standard eyeglass frames which accept a cold weather shield, which may be detachable from the glasses or may be permanently attached to the glasses. These shields are designed to provide enhanced cold protection to the eye area and proximal skin, over conventional glasses. In particular, the present invention addresses the need for an attractive and durable face shield which may be carried discreetly in a pocket or purse to use in public or private wherever needed for protection against cold weather is required.

The detachable shield and the standard glass frame system allow immediate utilization.

The shields also offer a sequence of contour size and fit.

The resiliency of the one-piece arcuate retaining member provides a clamping force by which the removable shield can be attached to the conventional eyeglass assembly. The side retaining members locate and attach the removable shield to the temple and/or cross members of conventional eyeglasses. Reliable securing elements are provided by resilience of the material used to construct the arcuate retaining member, particularly if higher-friction and anti-skid material is used to construct the side retaining members.

Additionally having a detachable shield allows use of specialized shields (such as those for day and evening use). Finally the shield is readily removable for thorough cleaning when needed.

The permanently attached shield has its benefits. Since the eyeglass frame and cold weather shield form a unit, the use of this unit is graceful, comfortable, stable, and conducive to continued use.

It is therefore an object of the present invention to provide a cold shield to give better cold protection for eyeglass wearers.

A second object of this invention is to provide a lightweight cold shield which fits onto a standard-style eyeglass frame.

A third object of this invention is to provide the eyeglass wearer with a single easy-to-carry and easy-to-use, comfortable, stable, one-piece functional unit—the eyeglasses and the cold shield forming one composite unit.

Another object of this invention is to provide a system which can easily be thoroughly cleaned.

Another object of this invention is to provide a cold shield which fits over substantially conventional frames so that the frames can be sized to fit comfortably and securely for individual facial dimensions. The shield fits to the face and to the frame to accommodate variations in facial shapes and glass contours.

A further object of the present invention is to provide a novel and improved cold shield for eyeglasses which provides an aesthetically pleasing appearance.

Still another object of the present invention is to provide a novel and improved cold shield for eyeglasses adapted for removable securement to temple regions of a wide variety of different eyeglasses without marring the eyeglasses.

Further scope of applicability of the present invention will become apparent from the detailed description given hereinafter. However, it should be understood that the drawings and the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow, and the accompanying following drawings which are given by way of illustration only, and thus are not limitations of the present invention.

DESCRIPTION OF PREFERRED EMBODIMENT

Figure 1:
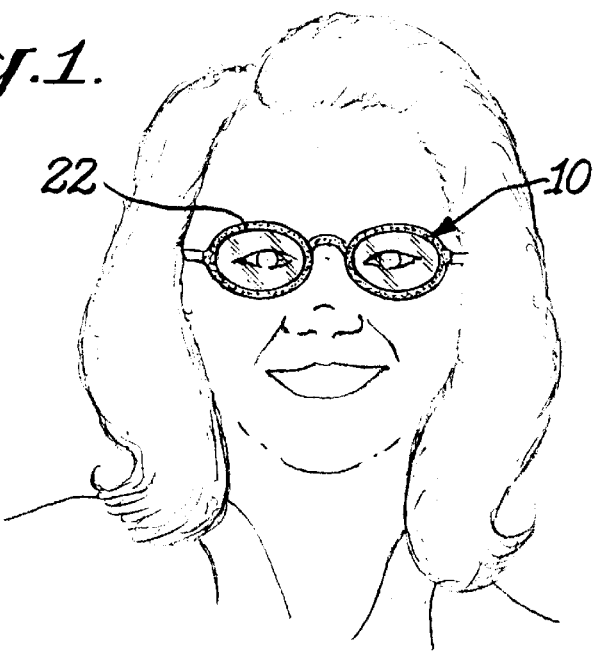
FIG. 1 is a pictural view illustrating an integrated embodiment of the instant invention in use.
Figure 2A:
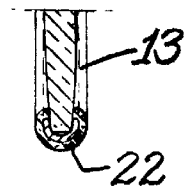
FIG. 2A is a cross-sectional view taken along line 2A—2A of FIG. 2 showing the shield.
Figure 2:
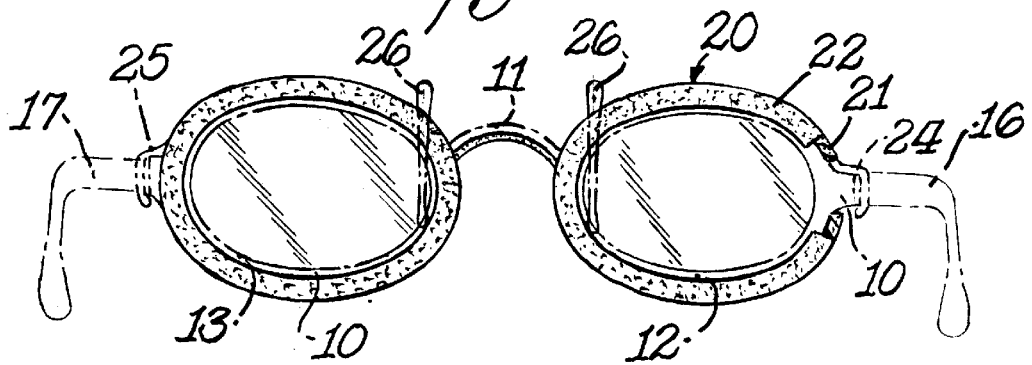
FIG. 2 is a front elevational view partially broken away showing the detachable embodiment of the eyeglass shield.

Referring to the various drawings, the cold shield eyeglass system of the instant invention is generally shown in use in FIG. 1. FIG. 2 shows the removable shield component (generally shown as numeral 20) removed from the eyeglass (generally shown as numeral 10).

As is shown in FIG. 2, the eyeglasses 10 in the first embodiment can comprise any standard frame and glass component. Generally, a crosspiece 11 is fixedly attached to and aligned with the left rim 12 and the right rim 13, each having an inner face in the direction of the face of the eyeglass wearer. The two rims are in a spaced apart arrangement with respect to each other such that the crosspiece 11 and the two rims define a space for the nose of the wearer. Mounted within the left and right rims 12, 13 are corrective lenses. Attached at each outer portion of the eyeglasses, which may be viewed as either the outer portion of the rims 12, 13, or at the outer portion of the crosspiece 11, depending on the style of the eye glasses, are standard hinges. Attached to each hinge are temple pieces 16 and 17 each of which terminates in an ear piece.

As is shown in FIG. 2, the removable weather shield 20 preferably comprises for use with eye glasses a flexible frame member 21 bent into an eyeglass-shaped configuration, and a covering 22 supported on the frame member 21. This frame member is lightweight, rigid enough only enough to maintain its shape and to support the covering 22, but flexible enough to be bent into a configuration that conforms with the eyeglass frame and the face of the wearer. It may be made from metal wire or relatively-flexible plastic such as styrene. The flexible frame member 21 has a linear dimension of about nine to thirteen inches, the length being sufficient only to maintain the covering 22 in proper configuration between the eyeglasses and the face of the wearer.

The covering 22 is preferably fabricated in the form of an elongated flexible sleeve having bore providing a through passageway to receive frame member 21. The bore of the covering 21 has a cross-sectional dimension which corresponds to the cross-sectional dimension of the frame member 21, preferably to snugly receive the frame member 21. The covering 22 may alternatively be affixed to the frame member by adhesives, by stitching loops from the covering around the frame member, or by any other conventional means. Covering 22 has a linear dimension which may be longer, equal to or shorter than that of the frame member 21. Covering 22, for example, can extend the entire length of the frame member 21, or may extend only around all or part of the circular portion of frame member 21 that abuts the eyeglass rims 12, 13 and not extend at the portion abutting the center portion of crosspiece 11.

The frame member 21 has means to attach the shield 20 to the eyeglass. The means can be of any form or type, provided only that the means permit the shield to be attached to the inner face of the eyeglasses 10 while permitting the combination of the eyeglasses 10 and shield 20 to be worn by the wearer. In the preferred embodiment, frame member 21 has retaining members 24, 25 and 26 projecting outwardly therefrom to secure the shield to the frame of eyeglass 10. As shown in FIG. 2, retaining member 24 is secured to the forward end of the first elongated temple piece 16 on one side of the glasses 10. A second retaining member 25 is secured to the forward end of the second elongated temple piece 17 on the other side of the glasses 10. As an alternative, or in addition to these retaining means, the shield may comprise retaining member 26 to secure the shield 20 to crosspiece 11 or the rim of the lens. Projecting from a portion of frame member 21 is a retaining outwardly projecting clip 26 positionally matching eyeglass crosspiece 11 or the rim of the lens.

The frame member 21 is made from plastic, and retaining means 24, 25 and 26 are preferably integrally-molded clips projecting outwardly and downwardly from frame member 21. The retaining outwardly projecting clips contact with their respective cooperative crosspiece 11 and/or temple pieces 16 and 17 of the eyeglass frame whereupon the clips releasably connect with the cooperative retaining pieces. Clips 24, 25 and 26 may be relatively short, or may be relatively long. With relatively short clips, it may be more difficult to establish a favorable location of the shield, due to the variations between the locations of the temple pieces and cross pieces relative to the wearer's eyes. With the greater length of the clips, the location of the removable shield can be adjusted by positioning clips 24, 25 and 26 anywhere between the upper and lower ridge portions of the clips.

Contemplated materials for the shield covering include, without limitation, fur, woven fabric, nonwoven fabric, fleece, cotton, wool, lycra and silk. The shield may also be made of more than one layer of material. In these multiple layered shields, the multiple layers can be attached together by lamination or stitching the layers of material together. The important characteristic of the material selected is that it be thermally insulating. Desirable characteristics include that the covering be soft to the touch, durable, and attractive. The preferred covering is fur, which may be synthetic or natural. The most preferred embodiment is natural mink fur, because it is non-shedding, provides instant warmth, and defines a stylish and attractive thermally insulating means that will be readily worn in the public. Such fur covering, along with possible matching or contrasting mittens, scarfs or headbands, may encourage persons to wear such shields. Simple foamed material which is not covered by fabric or fur is not desirable, because foam is structurally weak and prone to tearing, requires too much volume and does not provide the aesthetics that would encourage its use in normal public daily activities.

Preferably, shield 20 is attached to eyeglasses by clips 24, 25 and 26. In this manner, the removable shield 20 is fully supported. Alternatively, shield 20 may be supported only by center clip 26, or by side clips 24 and 25. One size of the clip-on shield can be attached to a wide variety of spectacles falling within a specific range of sizes, thus requiring only a limited range on clip-on shields to accommodate all sizes of spectacles, and, all variants within such spectacles, such as ocular spacing of the lenses of the spectacles, the perimetral shape and orientation of the lenses of the existing spectacles, including deviations in the frontal bowing of the existing spectacles.

The attachment of the removable weather shield 20 unto the eyeglasses 10 may be accomplished by first grasping the spaced opposed clips 24 and 25 and pushing the clip ends into the temple pieces and/or crosspiece 11 of the eyeglasses. Clip 26 can be similarly pushed unto crosspiece 11. The flexibility of the one-piece arcuate molded clips allows the removable shield to fit over a wide range of shapes, sizes, and styles of conventional eyeglass frames. Since the arcuate molded clips are still deflected from their relaxed position when it contacts the temple pieces and/or cross piece, they push in on the said pieces with a clamping force. This clamping force applied by the clips is transmitted through the temple pieces and/or crosspiece of conventional eyeglasses. Once in position, the clamping force will insure that the removable shield will remain in that position. The flexible nature of the clips allows them to conform to the shape of the exterior contact surface of temple pieces and crosspiece, thus maximizing the friction contact force by increasing the area of contact. Clips 24, 25 and 26 may also be fabricated of, for example, a high-friction, rubber like material, to provide additional means for both attaching and locating the removable shield. Removal of the shield may be accomplished by simply lifting the shield.

Figure 3:
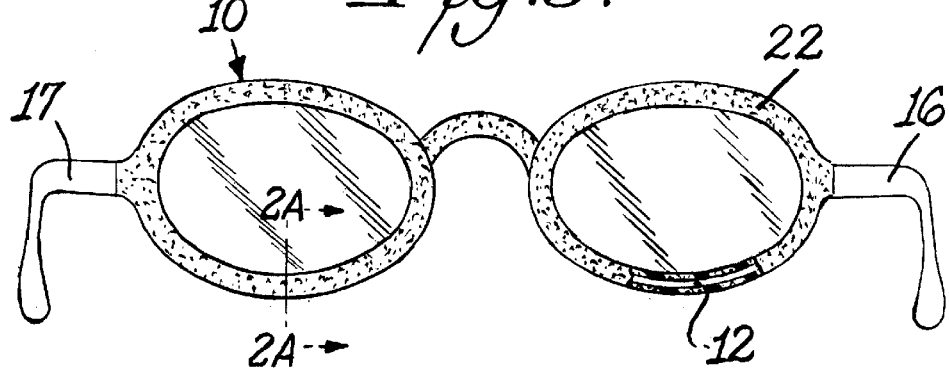
FIG. 3 is a front elevational view showing an integrated embodiment of the eyeglass shield of the invention.

FIG. 3 shows an integrated embodiment of the invention, wherein the covering 22 is permanently affixed to the eyeglasses 10. Covering 22 may be in the form of an open-ended sleeve that is affixed to the rims by friction or an adhesive between the eyeglass rims 12, 13. Alternatively, the covering may be mated to rims 12, 13 by stitches which hook around the covering material and the rims. The stitching material must, of course, not interfere with the position of the corrective lenses. The covering may surround the rims and/or the crosspiece 11, or be attached to the rims and/or the crosspiece only on the inside face.

It is contemplated that the removable shield or the covering in an integrated assembly will be offered in a variety of colors, surface textures, sizes and thermal insulations to meet particular demands of the wearer.

Thus, the cold weather shield provides comfortable thermal insulation around the sinus areas to reduce facial pain of sinusitis. The shield also provides a thermal barrier between relatively cold plastic or metal eyeglass frames as the sensitive sinus areas of the face. Another common problem with currently available glasses is fogging of the eye glasses during cold weather, caused by exhalation. However, the snug fit of the shield also minimizes fogging of eye glasses, because the shield inhibits the exhaled air from entering the eyeglass areas where the warm moist air can causes fogging. Fur also provides for some air circulation for the release and evaporation of any fogging of the glasses. The shield may also serve the function of filtration of air pollution and particulates, to filter out substances which assault the already sensitive eyes.

There are many variations of this system which can be made by those skilled in the art without departing from the inventive concepts expressed herein. Accordingly, the scope of my invention should be determined not by the embodiments described, but by the appended claims and their legal equivalents.

What is claimed is:

1. A cold weather system for protecting the eye areas of the wearer from the harmful effects of cold weather, comprising:
    (a) eyeglasses comprising:
        (i) a crosspiece having a left hand portion and a right hand portion,
        (ii) a left rim and a right rim, the right rim being fixedly attached to and aligned with the right portion of the crosspiece, and the left rim being fixedly attached to and aligned with the left portion of the crosspiece, the two rims defining a space between them for the nose of the wearer,
        (iii) a lens mounted in each rim,
        (iv) hinges attached to the left and right ends of the eyeglasses, and
        (v) two temple pieces; each of said temple pieces terminating at its further end in an earpiece for securing the eyeglasses to the ears of the wearer; and
    (b) thermally insulating shield abutting the inner face of said rims, comprising a covering selected from the group consisting of fabric, fur, and fabric-covered and fur-covered materials.

2. The cold weather system of claim I wherein said shield comprises an auxiliary clip-on for detachable attachment to a conventional eyeglass frame.

3. The cold weather system of claim 2 wherein said auxiliary clip-on for detachable attachment to a conventional eyeglass frame comprises a flexible frame member, and said thermal insulation is provided by a thermally insulating covering supported on said frame member.

4. The cold weather system of claim 3 wherein said frame member is bent into a configuration that conforms with the rim portion of the eyeglass frame, and said covering is in a form of a sleeve having an internal bore, with said frame member extending through at least a portion of said bore, and said frame member having clip members for detachable securement of said shield to said eyeglass frame, said clips providing a resilient bias acting to maintain said clip members in secure engagement with said eyeglass frame.

5. The cold weather system of claim 4 wherein said covering comprises fur.

6. The cold weather system of claim 1 wherein said shield comprises a covering affixed to the rim portion of said eyeglass frame.

* * * * *